United States Patent [19]
Degertekin et al.

[11] Patent Number: 6,070,468
[45] Date of Patent: *Jun. 6, 2000

[54] MICROMACHINED ULTRASONIC LEAKY WAVE AIR TRANSDUCERS

[75] Inventors: Fahrettin Levent Degertekin, Mountain View, Calif.; Abdullah Atalar, Bilkent Ankara, Turkey; B. T. Khuri-Yakub, Palo Alto, Calif.

[73] Assignee: The Board of Trustees of the Leland Stanford Junior University, Palo Alto, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/842,381

[22] Filed: Apr. 23, 1997

[51] Int. Cl.[7] ................................................. G01N 29/24

[52] U.S. Cl. ............................................... 73/644; 73/632

[58] Field of Search ........................... 73/644, 642, 632, 73/861.26, 861.28, 599

[56] References Cited

U.S. PATENT DOCUMENTS

| | | | |
|---|---|---|---|
| 4,838,127 | 6/1989 | Herremans et al. | 73/861.28 |
| 5,003,822 | 4/1991 | Joshi | 73/204.15 |
| 5,115,414 | 5/1992 | Atalar et al. | 73/642 |
| 5,129,262 | 7/1992 | White et al. | 73/599 |
| 5,159,838 | 11/1992 | Lynnworth | 73/644 |

*Primary Examiner*—John E. Chapman
*Attorney, Agent, or Firm*—Flehr Hohbach Test Albritton & Herbert LLP

[57] ABSTRACT

A method is disclosed for selecting characteristics (i.e. thickness-frequency product, length and material) of leakage plates used in ultrasonic transducers that transfer ultrasonic energy via leakage to fluid media with low acoustic impedances. High leakage efficiency and wide bandwidths are achieved by exciting the low order antisymmetric Lamb wave mode (A0) at the selected frequency in the leakage plate. Various actuator configurations that can be used to excite and detect the A0 mode in the leakage plate are described. Some embodiments employ reflector structures to intercept the leaky waves and reform them into beams normal to the plane of the leakage plate.

34 Claims, 13 Drawing Sheets

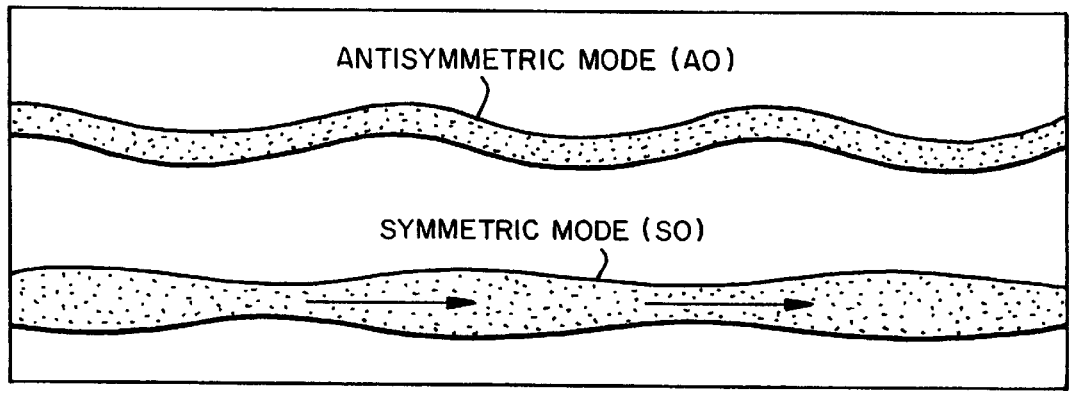
FIG_1
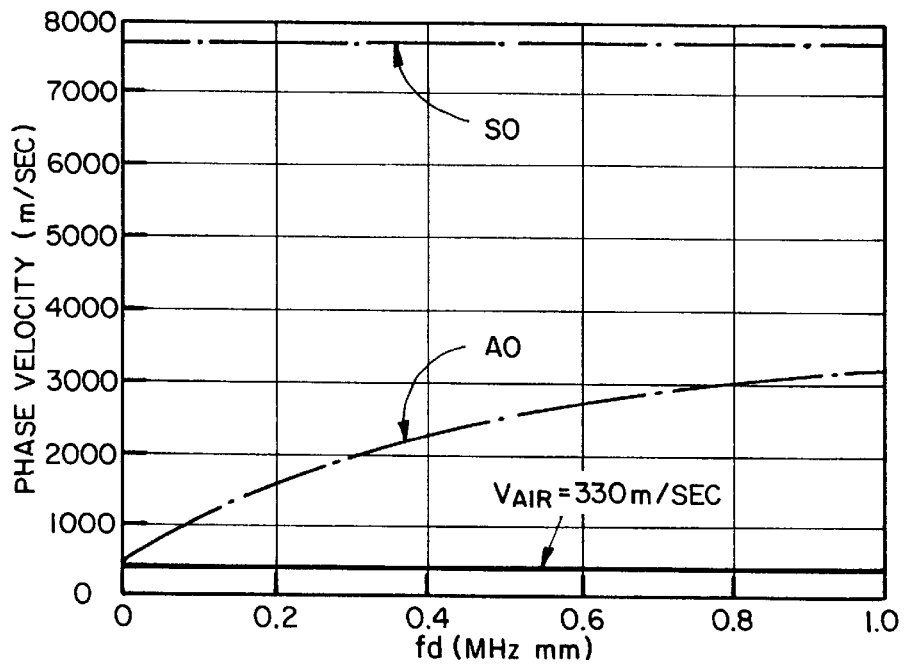
FIG_2

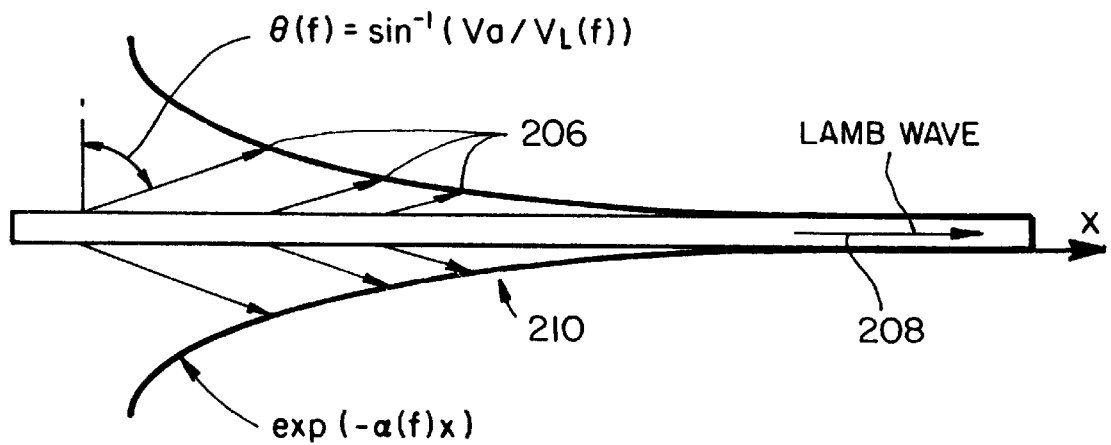
FIG_3
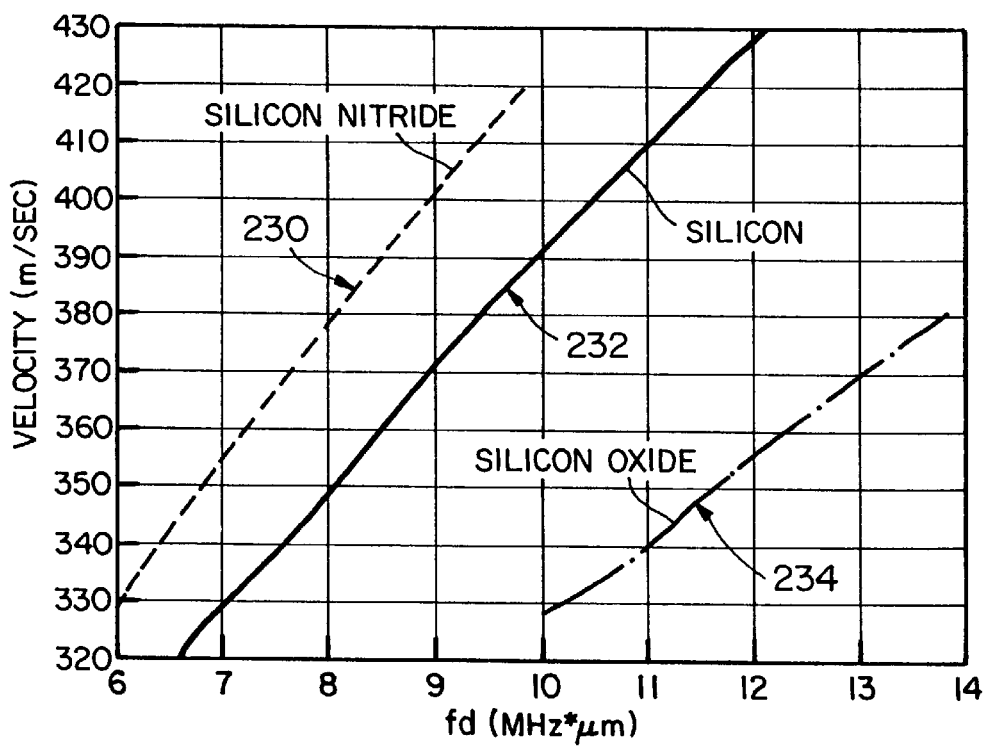
FIG_4

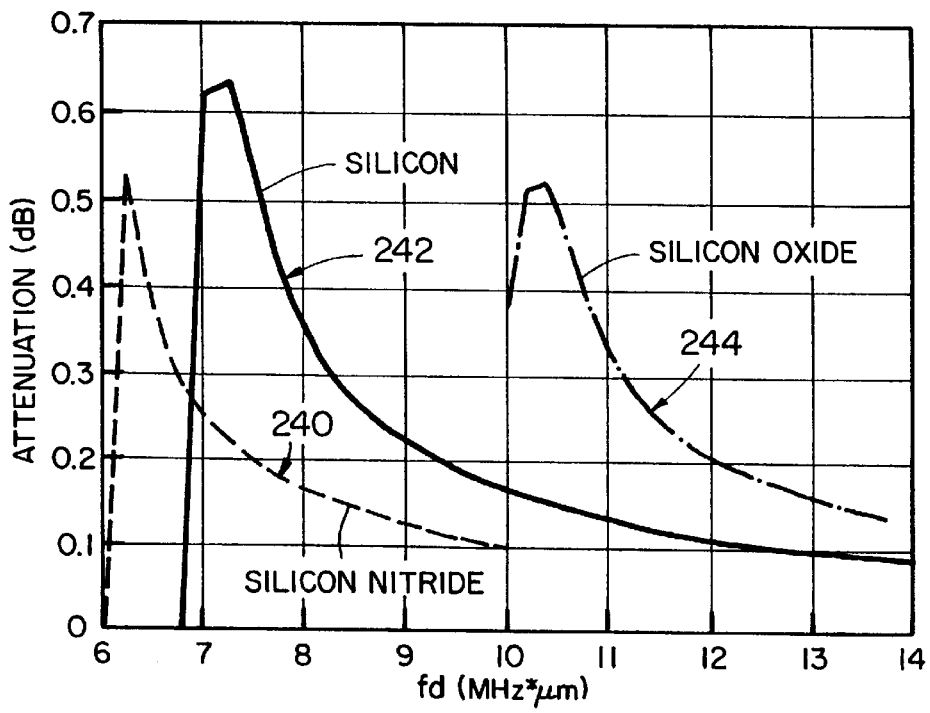
FIG_5
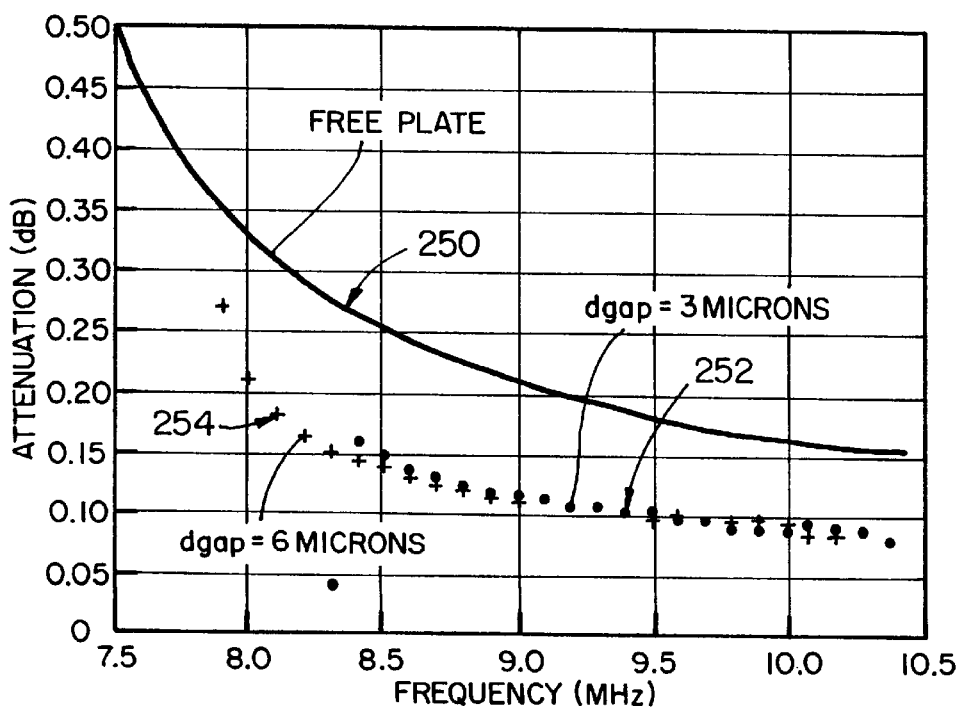
FIG_6

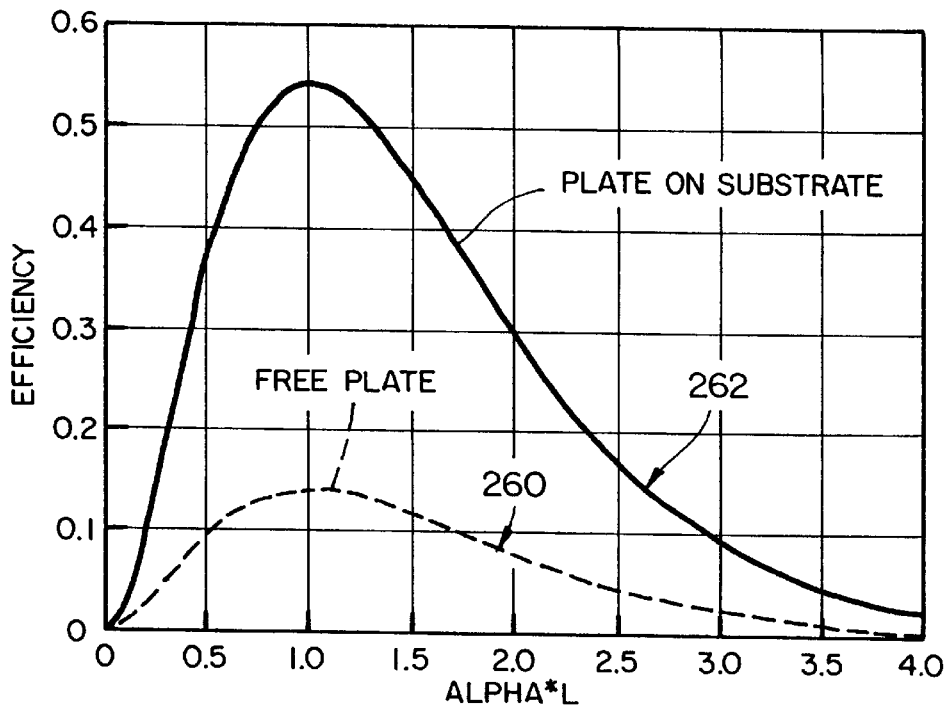
FIG_7
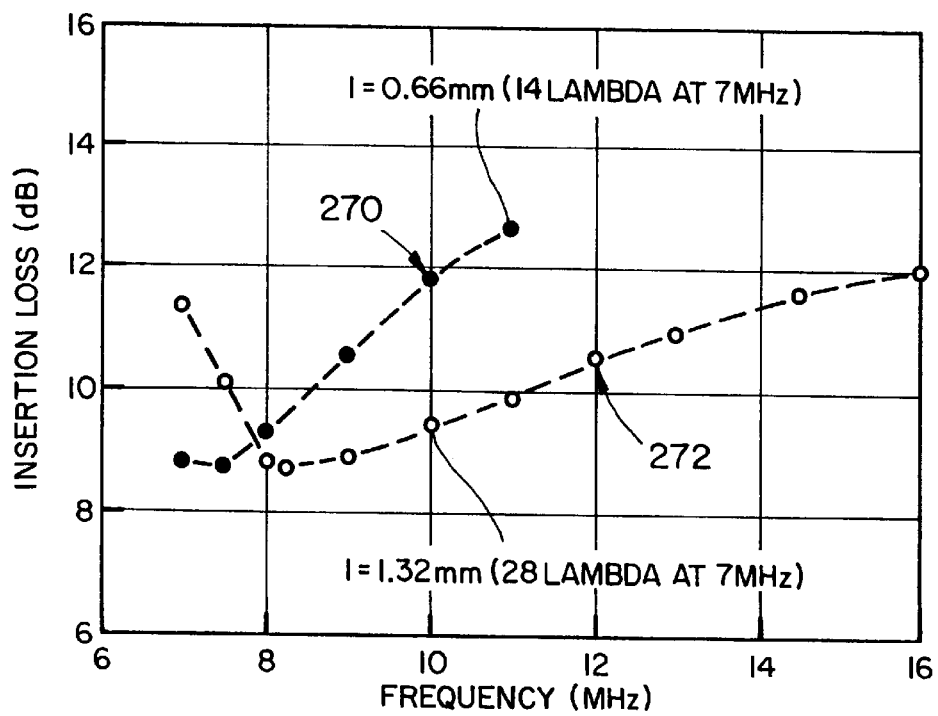
FIG_8

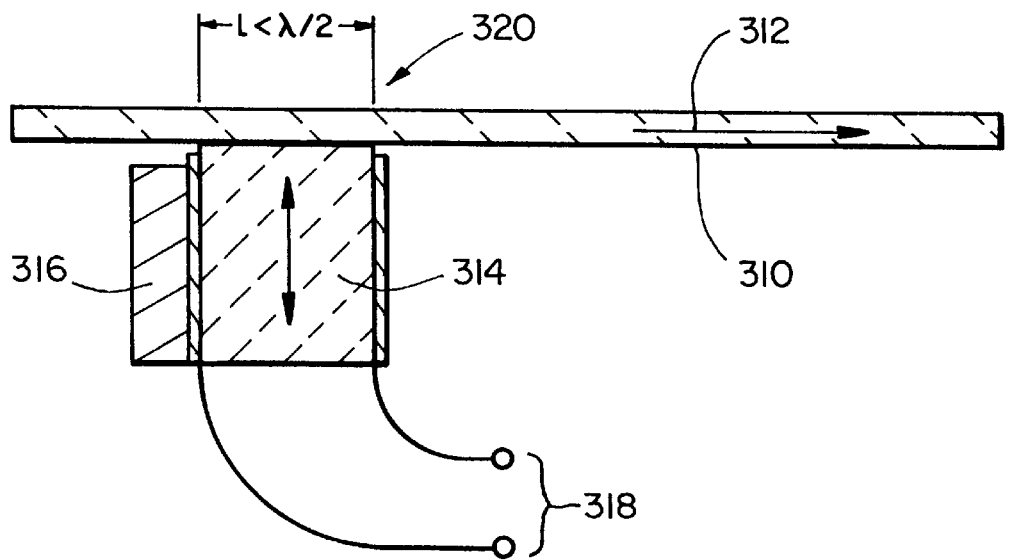
FIG_9A
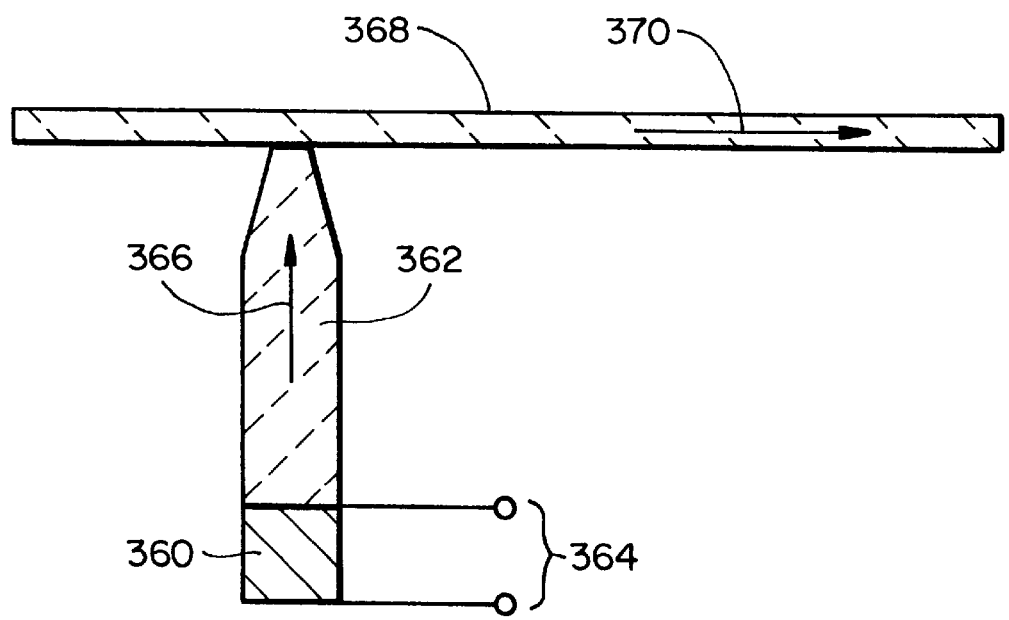
FIG_9E

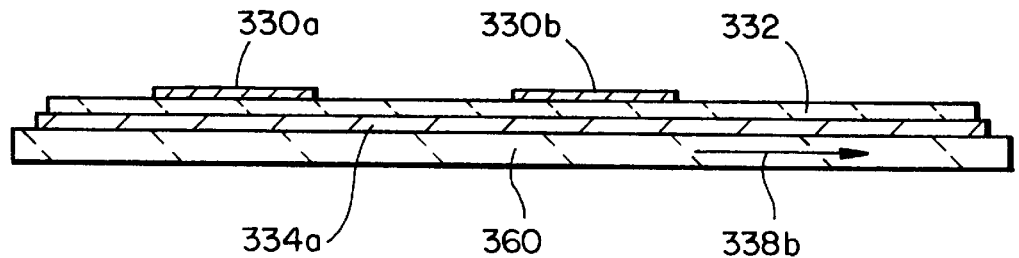
FIG_9B
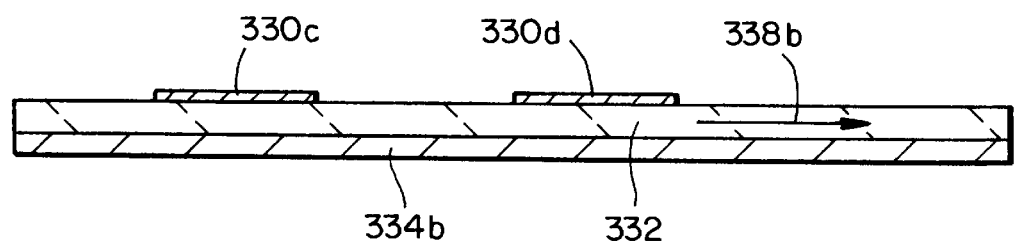
FIG_9C
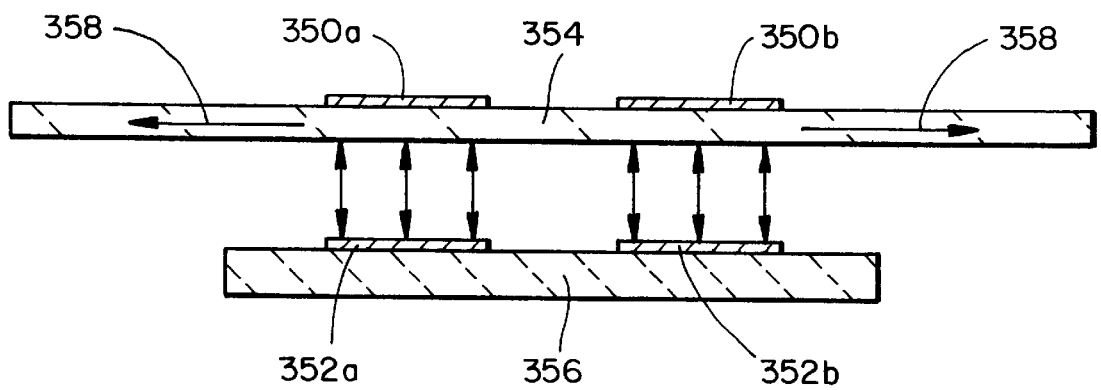
FIG_9D

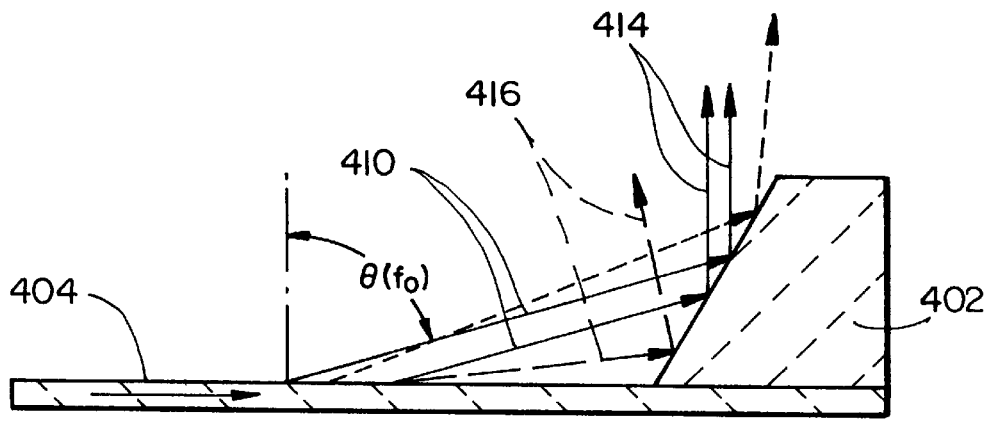
*FIG_10A*
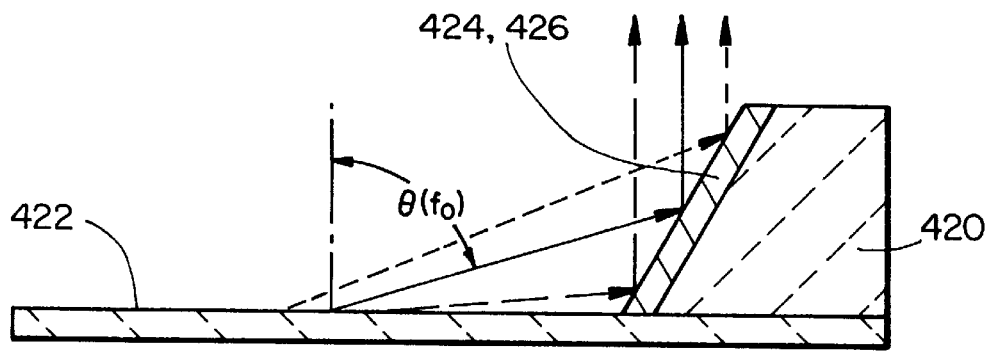
*FIG_10B*
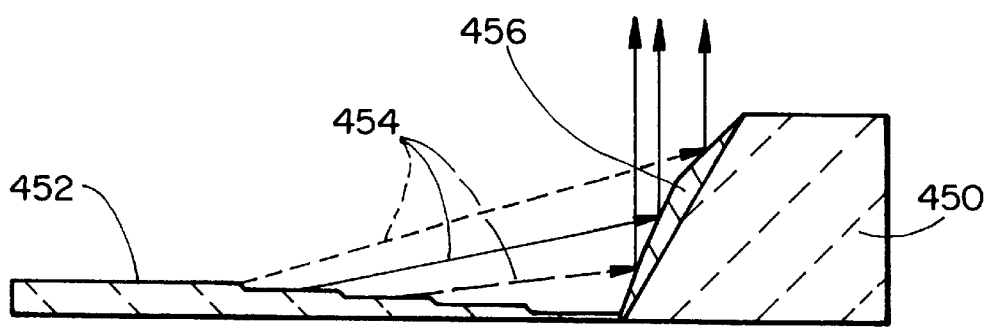
*FIG_10D*

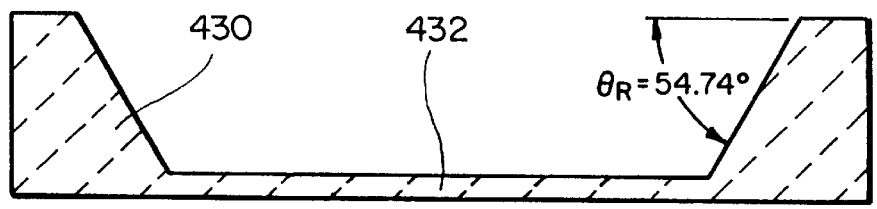
FIG_10C
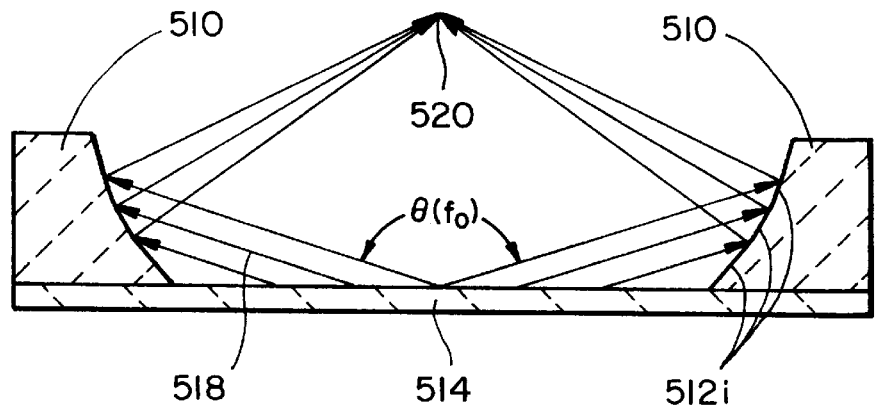
FIG_11A
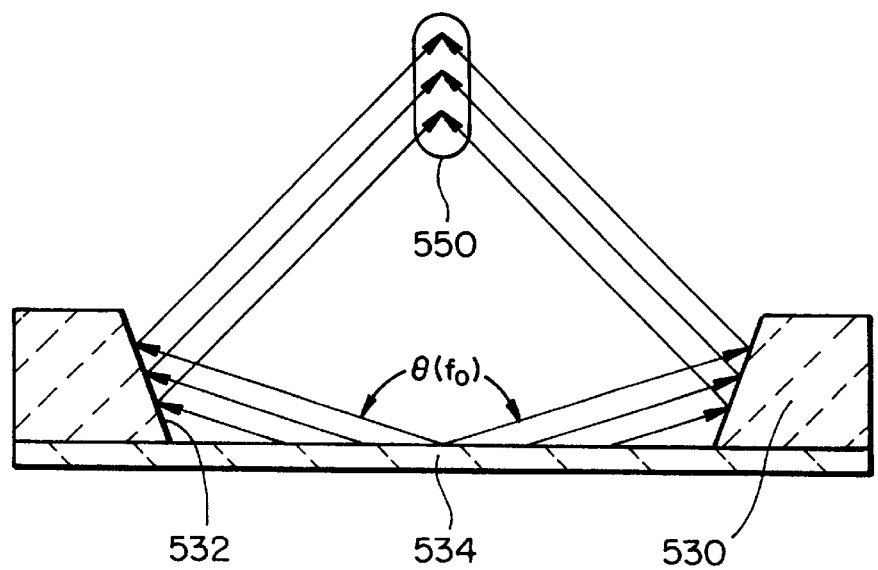
FIG_11B

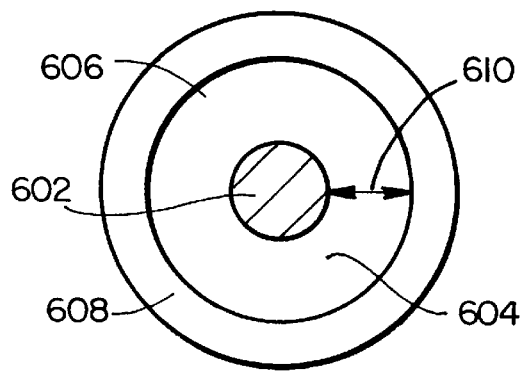
FIG_12A
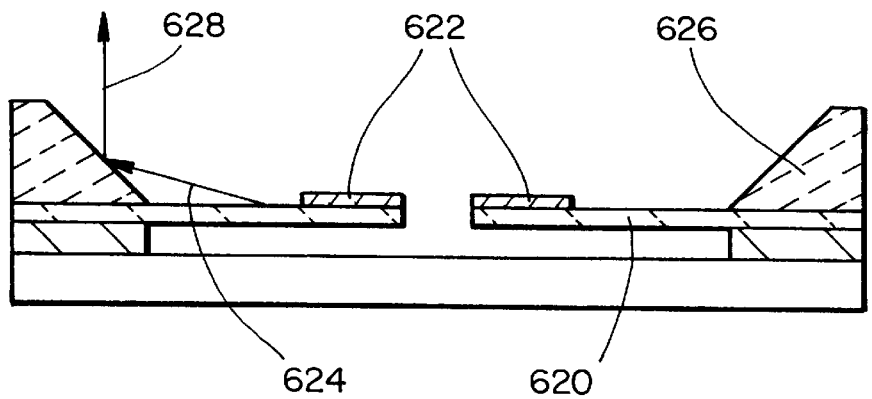
FIG_12B
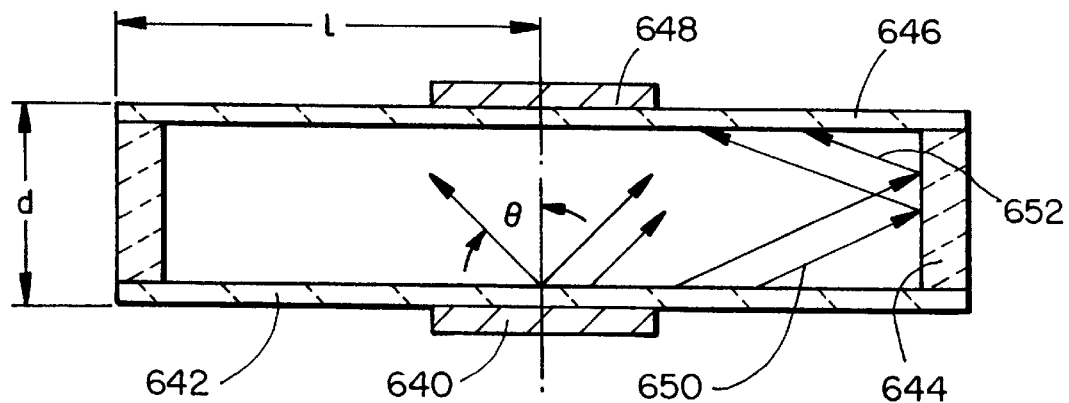
FIG_12C

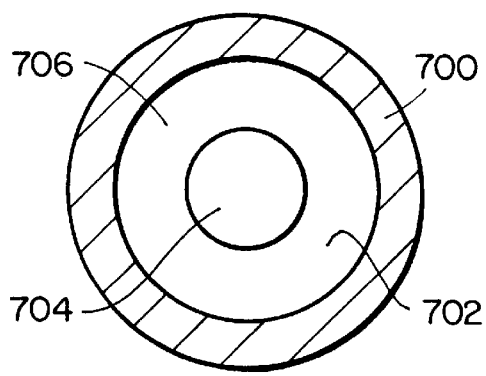 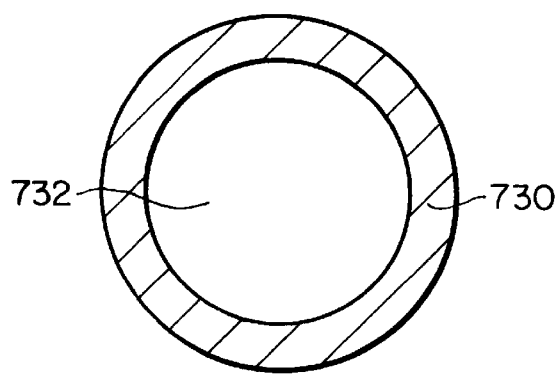
FIG_12D  FIG_12F
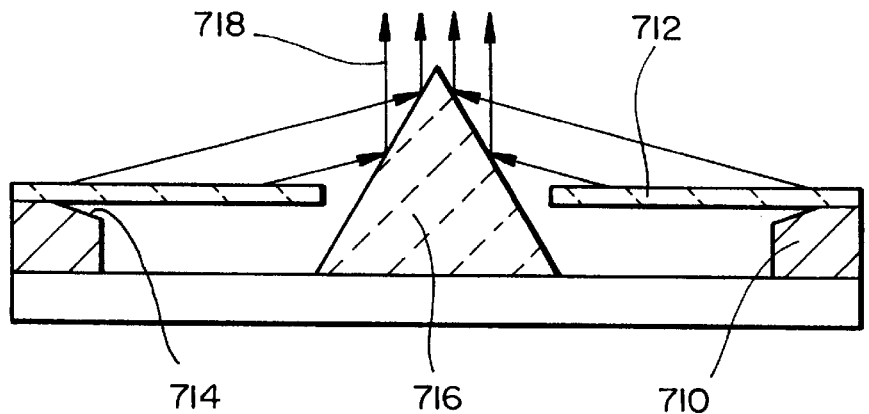
FIG_12E
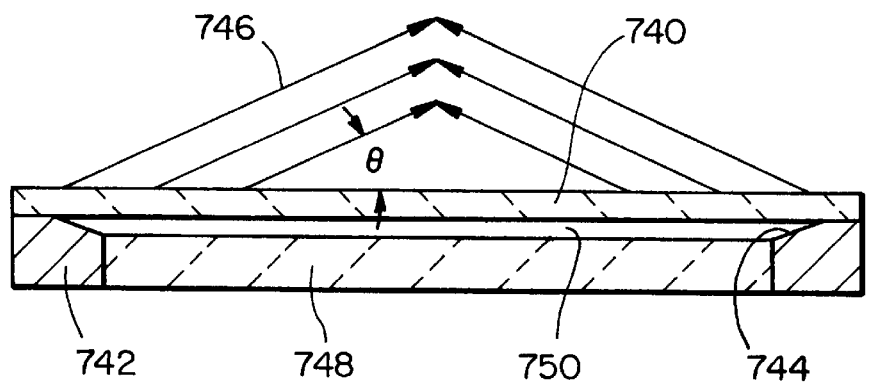
FIG_12G

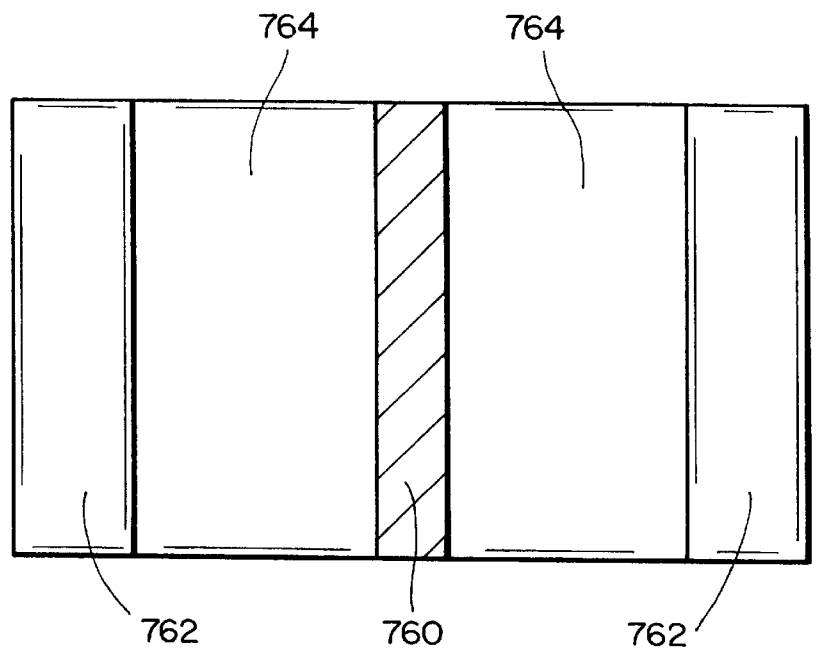
FIG_12H
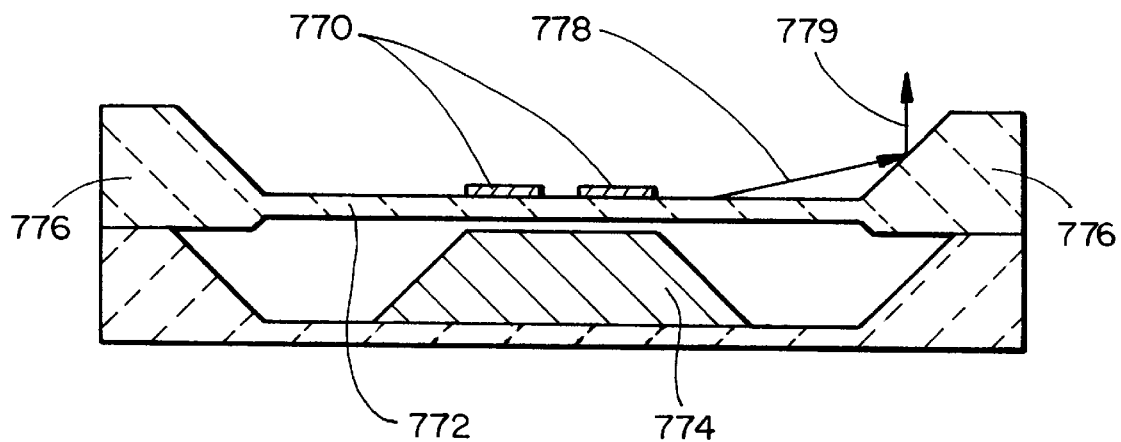
FIG_12I

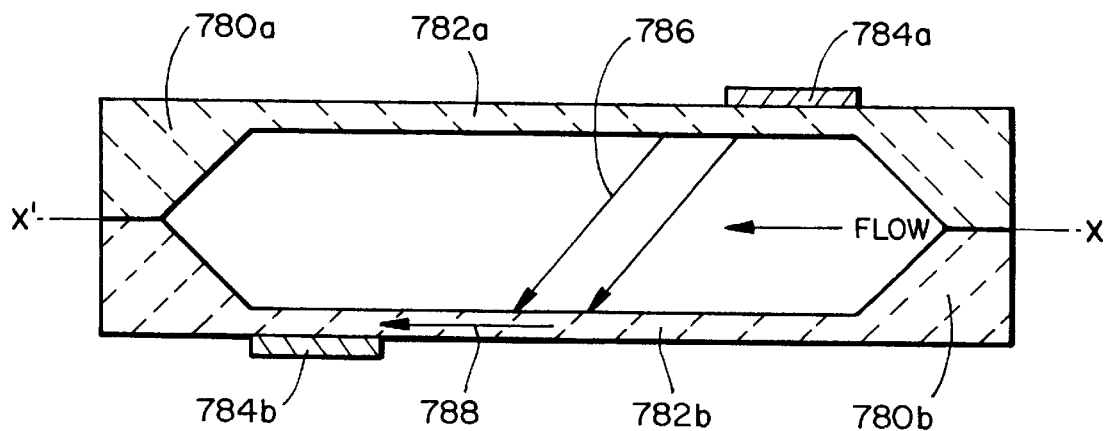
FIG_12J
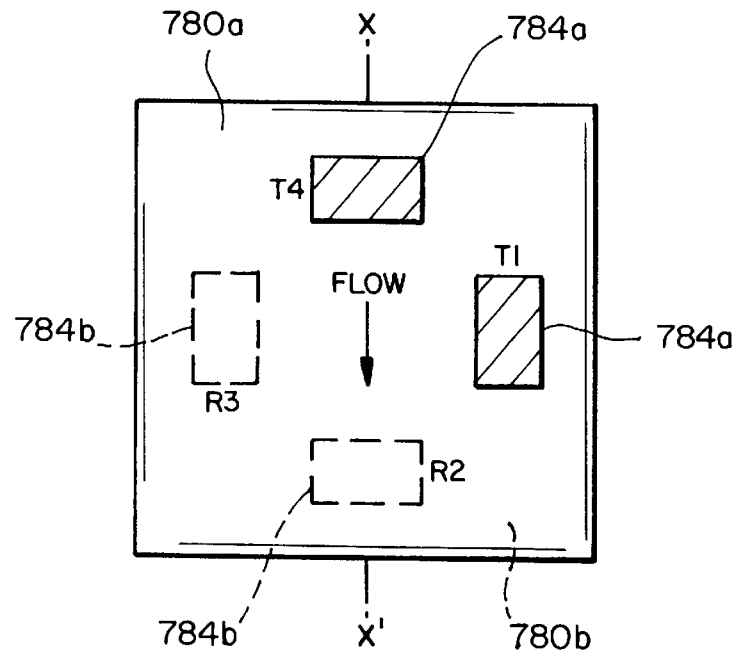
FIG_12K

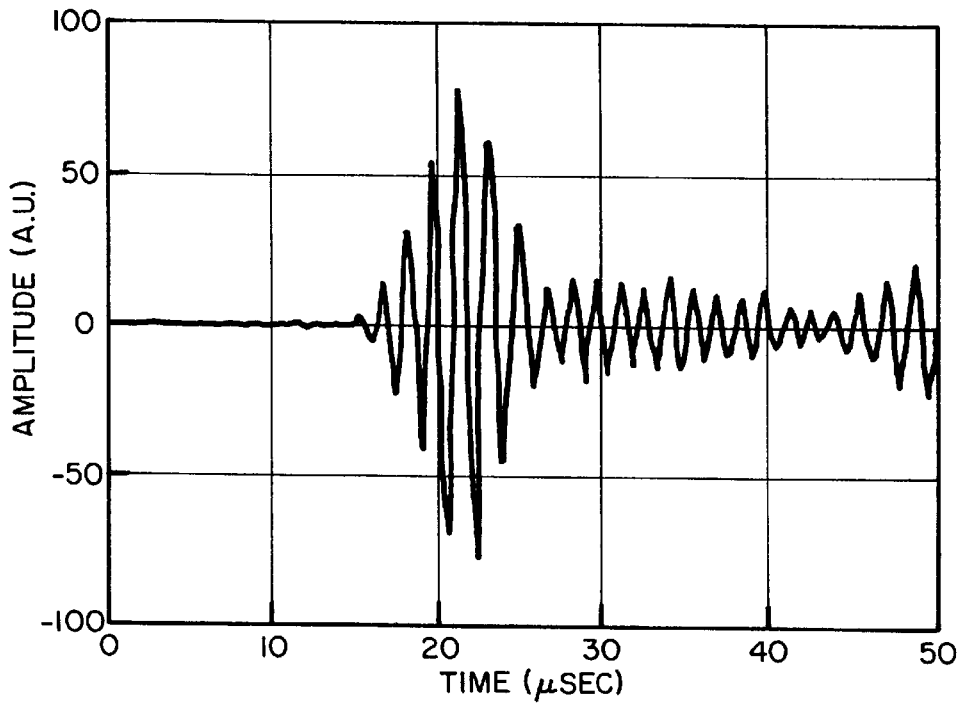
FIG_13A
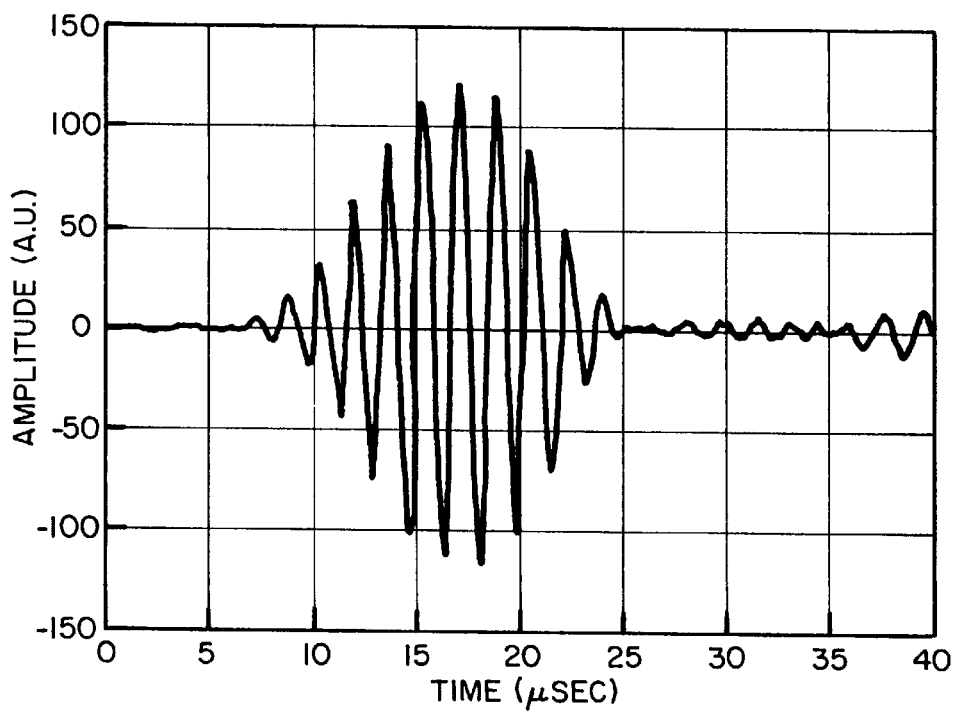
FIG_13B

MICROMACHINED ULTRASONIC LEAKY WAVE AIR TRANSDUCERS

The present invention relates generally to air transducers and, particularly, to ultrasonic leaky wave transducers wherein transmission of ultrasonic waves from an ultrasonic energy source to a surrounding fluid with a low acoustic impedance occurs by leakage.

BACKGROUND OF THE INVENTION

A typical application of ultrasonics involves exciting ultrasonic waves in a source using a transducer such as a piezoelectric transducer, transferring the ultrasonic waves from the source to a target medium, and then determining properties of a study object or the medium itself by measuring propagation characteristics of the ultrasonic waves.

One of the important problems in ultrasonics is how to transfer ultrasonic energy from sources of ultrasonic energy to fluid media such as air with a large bandwidth at frequencies in the MHz range. This problem is particularly difficult in air, due to its very low acoustic impedance (~400 Rayls) as compared to the common source impedances, which are on the order of $10^6$ Rayls for a piezoelectric transducer. Even in water, which has a much higher acoustic impedance (~$1.5 \times 10^6$) than air, several impedance matching layers between the source and the medium are required to achieve a reasonable transfer efficiency. Thus, there is a need for technology that provides for the efficient transfer of ultrasonic energy from high impedance sources to low impedance media without requiring a large number of matching layers.

Applications that require ultrasonic energy to be coupled into media of low acoustic impedance include medical imaging, nondestructive testing, process monitoring, pressure sensing, flow detection and robotic sensing. To achieve the necessary time and space resolution, these applications typically require ultrasonic signals in the MHz frequency range with high signal to noise ratio. Thus, there is a need for ultrasonic transducers that can efficiently couple high frequency ultrasonic waves into low impedance media with high signal to noise ratios.

SUMMARY OF THE INVENTION

The present invention is a collection of devices for coupling ultrasonic energy from a source to a fluid medium of lesser acoustic impedance via the process of ultrasonic leakage. In particular, the present invention encompasses a variety of devices that use the high energy leakage of the lowest order antisymmetric (A0) Lamb wave mode in thin micromachined plates to efficiently transfer ultrasonic energy to surrounding fluid media. These devices enable broad band operation in the MHz frequency range with high efficiency. The present invention also encompasses methods for fabricating the above-described transducers that are compatible with current silicon micromachining and integrated circuit (IC) technology.

Various embodiments include reflector structures that are configured to intercept the leaky waves and form those waves into a beam that is normal to the plane of the plate. Some of the reflector structures focus the leaky energy into a line, others focus the energy to a point.

The present invention is also a method for making a plate transducer for high bandwidth, high power ultrasonic leakage into fluid media having low acoustic impedance. This method involves selecting a transducer material for the plate transducer in which an A0 Lamb wave mode is dispersive with a range of phase velocities that approximately encompasses the velocity of sound in a fluid medium to which sound is to be coupled from the plate and that has high leakage attenuation, enabling small, micromachined plates to be fashioned from the transducer material. Given a particular transducer material, the next step involves selecting a plate thickness d. The product fd of the operating frequency f of the transducer and the thickness d determine the transducer's attenuation and bandwidth. In particular, based on the selected fd value, optimal attenuation can be achieved with narrow bandwidth or sub-optimal attenuation can be achieved with a wider bandwidth.

The efficiency of the transducer plate is a function of the product $\alpha l$ of the plate length l and a leak coefficient $\alpha$ associated with the transducer material. The efficiency is optimal when the product $\alpha l = 1$ and is suboptimal otherwise. As a result, the length l of the plate is selected in combination with the leak coefficient $\alpha$ so the transducer operates with the desired efficiency (i.e., optimal or sub-optimal). When configured according to this method, for a given frequency f and plate thickness d, a transducer plate will have narrower frequency response for the optimal efficiency mode than for the sub-optimal efficiency mode.

BRIEF DESCRIPTION OF THE DRAWINGS

Additional features of the invention will be more readily apparent from the following detailed description and appended claims when taken in conjunction with the drawings, in which:

FIG. 1 is an illustration of the schematic displacement profiles for the lowest order Lamb waves;

FIG. 2 is an illustration of dispersion curves for A0 and S0 Lamb waves;

FIG. 3 is a schematic illustration of ultrasonic energy leakage to air and important parameters;

FIG. 4 is a plot of phase velocity of A0 mode Lamb waves for selected micromachinable materials;

FIG. 5A is a plot of attenuation figures for the selected micromachinable materials of FIG. 4;

FIG. 5B is an illustration of a transducer plate with micro-pores 251 defined therein;

FIG. 5C is an illustration of a transducer plate with microstructures 253 defined therein;

FIG. 5D is an illustration of a transducer plate with variable thickness 257;

FIG. 5E is an illustration of a composite transducer plate;

FIG. 6A is a plot of attenuation figures for a 1 $\mu$m thick silicon plate for different substrate distances and for a free plate;

FIG. 6B shows a plate located close to a thick substrate that changes efficiency and attenuation of the plate;

FIG. 7 is a plot of air transducer efficiency as a function of leak rate $\alpha$ and transducer length l;

FIG. 8 is a plot of frequency response of a 1 $\mu$m thick silicon free plate in air;

FIG. 9A shows an actuator configuration that employs a piezoelectric transducer to excite Lamb waves in a transducer plate;

FIG. 9B shows an actuator configuration that employs interdigitial transduction to excite Lamb waves in the transducer plate;

FIG. 9C shows another actuator configuration that employs interdigital transduction to excite Lamb waves in the transducer plate;

FIG. 9D shows actuator configuration that employs electrostatic actuation excite Lamb waves in the transducer plate;

FIG. 9E an actuator configuration that employs a buffer medium coupled between a piezoelectric transducer and the transducer plate to excite Lamb waves in plate;

FIG. 10A shows a transducer that includes a single facet reflector bonded to the plate to transform leaky energy into a collimated beam;

FIG. 10B shows a transducer that includes a reflector bonded to the plate that includes multiple facets or a diffraction grating;

FIG. 10C shows a transducer that includes a micromachined single facet reflector and plate;

FIG. 10D shows a transducer that includes a micromachined, multi-facet reflector and variable thickness leakage plate;

FIG. 11A shows a reflector geometry for focusing leaky waves at a point;

FIG. 11B shows a reflector geometry for focusing leaky waves on a line;

FIG. 12A is a top view of a circularly symmetrical transducer with center actuation-detection and edge reflection;

FIG. 12B is a schematic view of an embodiment of the transducer configuration of FIG. 12A;

FIG. 12C is a schematic view of another embodiment of the transducer configuration of FIG. 12A;

FIG. 12D is a top view of a circularly symmetrical transducer with edge acuation-detection and center reflection;

FIG. 12E is a schematic view of an embodiment of the transducer configuration of FIG. 12D;

FIG. 12F is a top view of a circularly symmetrical transducer with edge actuation-detection and no reflection;

FIG. 12G is a schematic view of an embodiment of the transducer configuration of FIG. 12F;

FIG. 12H is a top view of a rectangular transducer with center actuation-detection and edge reflection;

FIG. 12I is a schematic view of an embodiment of the transducer configuration of FIG. 12H;

FIG. 12J is a schematic view of another embodiment of the transducer configuration of FIG. 12H;

FIG. 12K is a top view of the embodiment of FIG. 12J;

FIG. 12L is a schematic of an alternative embodiment of the system shown in FIG. 12J, in which the transducer halves 782 are separated;

FIG. 13A is a plot of the impulse response of a silicon plate transducer in air at 575 kHz; and FIG. 13B is a plot of the response of a silicon plate transducer in air at 575 kHz for a 5 cycle burst.

DESCRIPTION OF THE PREFERRED EMBODIMENT

The present invention achieves its advantages over the prior art by using selected Lamb wave modes (i.e., the lowest order, antisymmetric A0 mode) to achieve high energy leakage into media having low acoustic impedances. Before discussing the preferred embodiments, the properties of Lamb waves in general and the A0 mode in particular are now described.

The number of ultrasonic Lamb wave modes that can propagate in a free, solid plate is determined by the product (fd) of the Lamb wave frequency (f) and plate thickness (d). When the thickness d of the plate is smaller than the wavelength of propagation in the plate, only the two lowest order (A0 and S0) modes can propagate. The displacement profiles for the A0 and S0 modes in silicon are depicted in FIG. 1, which represents in schematic form the cross section of a plate in which the waves are propagating. FIG. 2 shows the phase velocity variations for the A0 and S0 Lamb wave modes in silicon. Referring to FIG. 2, note that the phase velocity of the S0 mode is independent from the plate fd and remains constant at a much higher level than the speed of ultrasonic waves in air ($V_{air}$). In contrast, the phase velocity of the A0 mode starts at about $V_{air}$ and increases with increasing plate fd. At all times, the phase velocity of the A0 mode is substantially less than the phase velocity of the S0 mode. These characteristics of the A0 mode are exploited by the preferred embodiments to provide high efficiency coupling of ultrasonic energy into air and other low acoustic impedance media.

When the solid plate is immersed in a fluid such as air, the ultrasonic waves start to radiate continuously to the surrounding fluid medium as shown in FIG. 3, which is schematic illustration of ultrasonic energy leakage 206 to air from a plate carrying Lamb waves 208. The rate of radiation depends on the characteristics of the mode. The pattern of this radiation (or energy leakage) and its direction can be calculated from the complex propagation constant k(f), which can be represented as the sum of a real part β(f) and an imaginary part α(f) as shown in Eq. (1).

$$k(f) = \beta(f) - j\alpha(f) \qquad \text{Eq. (1)}$$

The real part β(f) of Eq. (1) is related to the phase velocity of the Lamb wave in the plate $V_l(f)$ as shown in Eq. (2).

$$V_l(f) = \frac{2\pi f}{\beta(f)} \qquad \text{Eq. (2)}$$

The imaginary part α(f) of Eq. (1) is a leak efficiency coefficient that determines how rapidly the magnitude of the leaked energy $E_l(f)$ falls off with increasing x (where x denotes the distance a Lamb wave has traveled in a plate from the point of excitation). The relationship between α(f) and $E_l(f)$ is shown in Eq. (3).

$$E_l(f) = e^{-2\alpha(f)x} \qquad \text{Eq. (3)}$$

Given the velocity of the Lamb wave $V_l(f)$ and the velocity of sound in air $V_a$ (or any other surrounding medium), the angle of the leakage θ(f) can be determined according to Eq. (4).

$$\theta(f) = \sin^{-1}\left(\frac{V_a}{V_l(f)}\right) \qquad \text{Eq. (4)}$$

These equations show that when the phase velocity of the A0 mode Lamb wave $V_l(f)$ is close to the sound speed in the medium $V_a$, the leak rate reaches a maximum value that depends on the properties of the fluid and the plate material.

In light of these equations, it is apparent that the phase velocity of the Lamb mode should be dose to that of air for efficient coupling. Referring again to FIG. 2, the S0 mode has a phase velocity that is much higher than the sound velocity in air $V_a$ and is also nearly constant as a function of fd. As a result, the S0 mode cannot be used to leak ultrasonic energy into air or other low impedance media. In contrast, the A0 mode is highly dispersive (meaning that its phase velocity is highly variable as a function of fd) and, for selected fd, is quite dose to $V_a$. Consequently, the phase velocity of the A0 mode can be made arbitrarily close to $V_a$ by selecting the frequency of operation or the plate thickness properly. This selection results in a high ultrasonic energy leak rate, and as will be shown, in feasible dimensions for air transducers.

FIG. 4 depicts the phase velocity of the A0 Lamb wave mode as a function of frequency thickness product (fd) for widely used micromachined materials and for a useful range of fd values. These micromachined materials include silicon (curve 230), silicon nitride (curve 232) and silicon oxide (curve 234).

In FIG. 5, attenuation figures for silicon (curve 240), silicon nitride (curve 242) and silicon oxide (curve 244) are plotted in dB per wavelength as a function of the frequency thickness product Id. The absolute value and the shape of the attenuation curves determine the efficiency, size and bandwidth of transducers made from the respective materials. For example, the size of the leakage region needed to provide adequate ultrasonic energy is inversely related to a material's attenuation due to leakage. It is an object of the present invention to provide micromachined structures that efficiently leak ultrasonic energy into low impedance media. Thus, in order to decrease the size of the leakage region and the transducer, it is necessary to form the micro-machined structures from high attenuation materials. The curves of FIG. 5 show that silicon, silicon nitride and silicon oxide all have large attenuation figures, enabling those materials to be used in devices with dimensions feasible for micromachining. These materials have relatively low densities and, due to the ease with which they can be micromachined, their densities can be lessened to levels that are optimal for leakage attenuation. For example, micro-pores 251 (FIG. 5B) can be drilled in the transducer material or space-creating microstructures 253 (FIG. 5C) can be machined therein. In contrast, steel and brass, which have higher densities than silicon, silicon nitride and silicon oxide, are not satisfactory transducer materials given their poor leakage attenuation characteristics.

Note that it is not necessary that the material used to form the plate is homogenous and uniform. In fact, the plate material can be composite (FIG. 5E), piezoelectric and/or varying in thickness (FIG. 5D) to improve leakage and bandwidth. For example, by depositing silicon oxide 255a on silicon 255b (FIG. 5E) the attenuation characteristics can be changed between the corresponding homogenous materials (i.e., the silicon oxide and the silicon substrate). Also, by varying the thickness of the plate over the leakage region, the radiation pattern can be altered due to changes in the leakage rates, which can enhance the transducer's performance.

The attenuation values in FIG. 5 are valid for a plate in an infinite fluid medium. A thick substrate close to the plate can change these characteristics. Such closely separated structures are common in micromachining. For example, FIGS. 6A and 6B show the effect of a silicon half space (i.e., a gap between the substrate 270 and the plate 272 of less than half a wavelength) on the attenuation of the Lamb wave for various air gap thickness (dgap). In particular, attenuation curves 250, 252, 254 are shown for, respectively, a free 1 micron thick plate and the same plate with 3 micron and 6 micron gaps. It is observed that when $0.4 \lambda_{air} > dgap > 0.1 \lambda_{air}$, the attenuation rate is reduced to approximately one third of its free plate value in dB. This results in a larger transducer size, while the excitation efficiency is doubled since there is no energy leakage on the other side of the plate.

By plotting two-way power efficiency vs. leakage region length (l), the optimal transducer size can be determined. For example, FIG. 7 shows plots of efficiency versus the product of $\alpha$ and l (where $\alpha$ is defined in Eq. 3) at a single frequency for both free plate (curve 260) and plate over substrate (curve 262) cases. The optimum size/for the transducer should satisfy the relation $\alpha l = 1$, which is where the efficiency curves 260, 262 we at their maximum. For this optimum value, the two way insertion loss can be as low as 8.7 dB for a free plate and 2.7 dB for a plate over substrate. Since the efficiency curves have a relatively broad peak, transducers of the optimum size will have a wide bandwidth of operation.

As transducer leakage is a function of the frequency-thickness product fd, the center frequency of the transducer can be adjusted by changing the thickness of the plate. This enables a particular transfer efficiency to be achieved for different desired frequency ranges. Also, by selecting the region of the attenuation curves (FIG. 5) in which the transducer is to operate, different transducer bandwidths can be obtained. In particular, a small transducer with narrow bandwidth results if it is selected to operate in the region of FIG. 5 where the attenuation is very high (e.g., at about fd=7.25 for silicon). For broadband operation, the region of the attenuation curve where the variation is-small and the absolute value is still high (e.g., between fd=8 and 9 for silicon) should be chosen as depicted in FIG. 5. Thus, a transducer of sub-optimal length l (fd=8–9 for silicon) gives near optimum efficiency with a wider frequency range than a transducer of optimal length l (fd=7.25 for silicon).

The attenuation curves of FIG. 5 can also be used to estimate the dimensions of a typical device. For example, considering a 1 µm thick free silicon plate, a maximum value of 0.65 dB attenuation per wavelength of the A0 mode occurs at about fd=7 MHz*µm, where the phase velocity of the A0 mode matches the speed of sound in air $V_{air}$. From this fact, the optimum transducer size/can be determined to be 14 wavelengths, corresponding to a length of 0.66 mm (derived using the standard value for $V_{air}$ of 331 m/sec and a frequency f of 7 MHz in the equation V=λf, which relates wavelength, frequency and phase velocity). A plate of this size (1 µm×0.66 mm) is easily realizable by micromachining techniques. How the length in wavelengths is derived from the maximum attenuation value is now described in relation to FIGS. 5.and 7.

At each frequency f there is a specific leak rate $\alpha(f)$. For that leak rate $\alpha(f)$ the optimum transducer size $l_{opt}(f)$ is determined according to Eq. (5). This relationship between $\alpha$ and $l_{opt}$ is apparent from FIG. 7, where the product of $\alpha$ and l is plotted on the x-axis.

Attenuation per wavelength $\alpha[dB]$, which is plotted vs the product of frequency, f, and thickness, d, in FIG. 5, can be expressed as in Eq. (6) below.

$$\overline{\alpha}[dB] = -20\log_{10}(e^{-\alpha(f)\lambda}) = 8.68\alpha(f)\lambda \qquad \text{Eq. (6)}$$

where $$\left(\lambda = \frac{V_{phase}}{freq}\right)$$

The relationship a and attenuation per wavelength is defines as shown in Eq. (7).

$$\alpha(f) = \frac{\overline{\alpha} \, [\text{dB}]}{8.68 \times \lambda} \qquad \text{Eq. (7)}$$

As a result, given a maximum attenuation per wavelength selected from FIG. 7, the optimal transducer size $l_{opt}(f)$ for a frequency f (with a corresponding wavelength $\lambda$) can be determined with Eq. (8).

$$l_{opt}(f) = \frac{1}{\alpha} = \frac{\lambda \times 8.68}{\text{Attn per wavelength}} \qquad \text{Eq. (8)}$$

FIG. 8 shows plots of insertion loss (in dB) for a 1 μm thick silicon plate as a function of frequency (in MHz) for two different transducer sizes, a 1.32 mm plate (curve 272) and a 0.66 mm plate (curve 270). These curves illustrate the efficiency-bandwidth-size trade-off for the transducers. The curve 270 shows the insertion loss for the optimum transducer size (14 $\lambda$) where the frequency-thickness product fd=7 Mhz*μm. From this curve the fractional 3 dB bandwidth (the bandwidth at the 3 dB point divided by the center frequency) can be estimated to be approximately 35%. In comparison, the curve 272 shows the insertion loss for a suboptimum transducer size (28 $\lambda$), for which the estimated fractional 3 dB bandwidth is more than 78%. Thus, the overall bandwidth is mainly limited by the A0 mode excitation mechanism. Note, however, that the efficiency and bandwidth values from the curves 270, 272 may be hard to achieve in practice due to limitations such as alignment problems, air saturation, etc.

In the present invention nearly all ultrasonic energy is transferred to air through leakage from the transducer. The main limitations on the ultrasonic power level in air include the A0 mode Lamb wave excitation/actuation mechanism (i.e., the means used to excite ultrasonic waves in the transducer) and the nonlinear behavior of air at high ultrasonic signal levels.

Referring to FIGS. 9A–9E, there are shown schematic illustrations of five Lamb wave excitation/actuation mechanisms that are among those that can be employed by the present invention. Each of these mechanisms embodies the well known fact that the most efficient method for exciting the A0 Lamb wave mode involves applying asymmetric normal traction to the surface of the plate (i.e., displacement of the surface of the plate perpendicular to the plane of the plate). This method is especially effective for the low fd values of the present invention at which the normal particle velocity is the dominant factor in the power transport (i.e., generation of the A0 mode). The respective mechanisms of FIGS. 9A–9E include direct piezoelectric material bonding, interdigital transduction, electrostatic actuation, and piezoelectric transducer-buffer medium combinations. These mechanisms are described below. For detection of the normal plate movements caused by Lamb wave modes propagating in the plate, the excitation schemes can be used directly or some modifications can be employed to increase sensitivity. For example, a capacitance detector can be employed with an electrode gap smaller than the one in the actuator. The power loss due to the nonlinearity of air can be prevented by distributing the power over a large area, thereby reducing the intensity in air.

FIG. 9A shows a Lamb wave excitation mechanism employing direct bonding of a piezoelectric actuator 314 to a transducer plate 310. Upon electrical excitation of the actuator 314 via contacts 318, normal movements of the plate 310 are initiated at the interface 320, which is less than $\lambda/2$ wavelengths wide. These normal movements are translated to a Lamb wave A0 mode propagating in the plate 310. A backing 316 is attached to one side of the piezoelectric actuator 314 to damp other than vertical vibrations in the actuator 314, which increases the ultrasonic energy coupled into the plate 310.

Two different excitation mechanisms that use interdigital transduction (IDT) are shown in FIGS. 9B and 9C. Both embodiments include electrically conductive IDT fingers 330 bonded to one side of a piezoelectric plate 332. In FIG. 9B, the piezoelectric plate 332 is laid on a non-piezoelectric plate 334a. In FIG. 9C, the piezoelectric plate 332 is laid on a metal plate 334b. In each of these embodiments, according to well-known principles of interdigital transduction, the fingers 330 are used to set up Lamb waves in the piezoelectric plate 332. The spacing between the fingers 330 determines the frequency and bandwidth of the Lamb waves. The Lamb waves in turn set up normal vibrations in the piezoelectric plate 332 whose frequency is determined by the frequency of the Lamb waves.

In the embodiment of FIG. 9B, a transducer plate 336 underlies the non-piezoelectric plate 334a. In response to the normal vibrations of the piezoelectric plate 332 and the underlying plate 334a, the Lamb wave A0 mode 338a is set up in the plate 336. In contrast, the embodiment of FIG. 9C has no underlying transducer plate 336. Instead, the Lamb wave 338b is induced to travel in the piezoelectric plate 332.

In the embodiment of FIG. 9D, which employs an electrostatic actuation mechanism, a pair of electrodes 350 are bonded to one side of a flexible transducer plate 354 and another pair of electrodes 354 are bonded to one side of a rigid beam 356. A modulated electrostatic potential is placed across the electrodes 350 and 352, which induces normal movements and Lamb waves 358 in the transducer plate 354 only. The rigid beam 356 acts as a substrate, enhancing transducer efficiency.

FIG. 9E shows an embodiment wherein a piezoelectric transducer 360 is excited using electrodes 364 to generate longitudinal waves 366 in a buffer rod 366. The longitudinal waves 366 are coupled by the pointed tip of the buffer rod 366 into a transducer plate 368 as Lamb waves 370 via the mode conversion process.

Having described the various mechanisms that can be employed in the present invention to excite the A0 mode in a transducer plate of the appropriate dimensions, various embodiments are now described that modify the pattern of leakage from the transducer and/or provide broadband transducer operation.

As shown in FIGS. 3 and 4, the transducer radiation (i.e., leakage) occurs in a short distance x for $\theta(f) \equiv 90°$ (where $V_l$ (f) is approximately equal to $V_a$) and is reasonably efficient for $\theta(f)$ in the 45°–90° range. The radiated field is concentrated at the surface of the plate and is diffracted in a short distance. Using specially designed reflecting structures configured to intercept the radiation, the present invention converts the radiated field to a less diffracting and more useful form for efficient ultrasonic transduction. Depending on the application, these reflectors can be micromachined or regularly machined. Some preferred reflector structures are now described in reference to FIGS. 10 and 11.

Referring to FIG. 10A, there is shown an embodiment wherein a single planar reflector 402 with an angle $\theta_R$ defined according to Eq. (9) is coupled to one side of a transducer plate 404.

$$\theta_R = 90° - \frac{\theta(f_0)}{2} \qquad \text{Eq. (9)}$$

The reflector 402 converts the leaky ultrasonic field 410 at a frequency $f_0$ from the transducer 404 to a collimated beam with in-phase components 414 propagating perpendicular to the transducer plate 404. Other frequency components 416 are spread by the reflector 402 at angles other the angle $\theta_R$ due to the phase velocity dispersion phenomenon. I.e., because phase velocity is a function of frequency (Eq. (2)) and the angle at which leakage occurs is a function of the phase velocity (Eq. (4)), the leakage angle $\theta(f)$ is a function of frequency.

Referring to FIG. 10B, there is shown a reflector 420 bonded to the transducer plate 422 that is modified to prevent this spreading and, as a result, provides broader bandwidth and higher signal to noise ratio. This can be realized by a reflector with multi-facets 424 (as shown in FIG. 10D) that account for the varying leak rates (and angles) or a diffraction grating 426 that undoes the dispersion.

The embodiments of FIGS. 10A and 10B employ reflectors that are bonded to the transducer plate. Similar reflector structures and leakage plates can also be micromachined from a single material.

Referring to FIG. 10C, there is shown a preferred reflector geometry that can be implemented as part of an all micromachined transducer on silicon (i.e., a transducer wherein the plate and the reflector structures are fabricated from the same piece of silicon). Using the anisotropic etching properties of <100> oriented silicon crystal on the <111> plane, a linear planar reflector 430 with $\theta_R=54.74°$ can be fabricated in conjunction with a <100> plate 432. A reflector 430 so configured will redirect leaky waves with $\theta=70.5°$ to a beam perpendicular to the transducer plate. The thickness of the plate 432 can be varied to modulate the leaking field as in the plate 452 of FIG. 10D. Referring to FIG. 10D, the leaking field 454 can be reflected by a multi-facet reflector 456, resulting in a higher bandwidth as described in reference to FIG. 10B.

Note that the leaking field acts as a plane wave in case of a rectangular geometry or as a diverging conical wave in a circularly symmetrical geometry. Consequently, the leaking field incident on a reflector can be focused at a point or on a line by suitable reflector structures depicted in FIGS. 11A–11B.

Referring to FIG. 11A, a reflector 510 can be configured with multiple reflecting surfaces 512-$i$ whose respective reflecting angles $\theta_i$ (where $\theta_i$ is defined relative to the plane of the plate 514) are selected to focus the leaky energy 518 at a leak angle of $\theta(f_0)$ at a single point 520.

Alternatively, a reflector 530 can be configured with a single reflecting plane 532 whose angle $\theta$ is selected to focus the leaky energy at a leak angle of $\theta(f_0)$ onto a single line 550 perpendicular to the plane of the plate 534.

The transducer plate designs, A0 mode excitation and detection schemes and different reflector configurations described above can be variously combined to form efficient, broadband ultrasonic transmitters and receivers in fluids. A collection of preferred transducer configurations are now described in reference to FIGS. 12A–J. Each of the embodiments illustrated in FIGS. 12A–J includes elements performing at least two of three distinct functions: actuation-detection, reflection (in some cases, the reflection function can be eliminated) and ultrasonic leakage. In particular, the configurations shown schematically in FIGS. 12A–J are suitable for micromachining from materials such as silicon. Also, in each configuration using a reflector, the distance between the actuation region and the reflector is determined according the efficiency arguments presented above in reference to FIGS. 3, 4, 10 and Referring to FIG. 12A, there is shown an overhead view of a circularly symmetrical transducer configuration including a center actuator 602 that excites the A0 mode in a leakage plate 604. The resulting ultrasonic energy leaks from a leakage region 606 and is reflected by an annular reflector structure 608 spaced an optimal distance 610 from the actuator 602. This particular configuration can be used as shown in FIGS. 11A and 11B to form point-focused or line-focused beams.

Referring to FIG. 12B, there is shown one possible configuration of toe center-actuated transducer of FIG. 12A. This configuration makes use of electrostatic ring actuation to excite the A0 mode in an annular plate 620. The center of the annular plate 620 is unsupported and has mounted thereon an annular actuator 622 that, in response to electrostatic potentials of the appropriate frequency and magnitude, causes A0 mode flexural waves to be excited in the plate 620. As described above, ultrasonic energy 624 leaking from the plate 620 is transformed by an annular reflector 626 into a beam 628 perpendicular to the plane of the plate 620.

Another center-actuated transducer configuration is shown in FIG. 12C. This configuration employs an actuator 640, an actuator plate 642, a cylindrical reflector 644 (or multiple cylindrical section reflectors 644$i$), a detector plate 646 and a detector 648. In this configuration, ultrasonic energy is excited in the actuator plate 642 by the actuator 640 through one of the disclosed ultrasonic excitation mechanisms. Energy 650 leaking from the actuator plate 642 is reflected by the reflector 644 and the reflected energy 652 is coupled into the detector plate 646, where it sets up flexural waves. These waves are then coupled to the detector 648, which can then be used to generate corresponding electrical signals. This configuration can be used for flow/pressure metering of fluids flowing between the plates 640, 646, whose properties influence the amplitude and velocity of the transmitted and reflected energy 650, 652 and the resonance frequency of the actuator detector pair 640, 648.

The transducer of FIG. 12C operates at maximum efficiency when the plate separation d, half-width/and leak angle e satisfy Eq. (10). D can be a multiple of the value computed according to Eq. (10). For example, at f=7.5 MHz and with the half-width/=1 $\mu$m, for optimal efficiency d can be set to N×10.48 mm (where N is an integer constant). In an alternate embodiment, the reflectors 644 can be widely separated to enable flow pressure metering to be performed over correspondingly longer distances.

$$d=2/(\tan\theta)^{-1} \qquad \text{Eq. (10)}$$

FIG. 12D shows the overhead view of another transducer configuration employing edge actuation-detection and center reflection. In this configuration, an annular actuator-detector 700 excites and detects ultrasonic energy in a plate 702. A central reflector 704 reflects ultrasonic energy that leaks from a leakage region 706 and forms a beam that is roughly perpendicular to the plane of the plate 702.

A particular embodiment sharing the geometry of FIG. 12D is shown in FIG. 12E. In this embodiment, a piezoelectric ring 710 is bonded to one side of a transducer plate 712. The inner edge 714 of the piezoelectric ring 710 is not in contact with the bottom surface of the transducer plate 712. This enables the transducer plate 712 to flex in response to normal ultrasonic vibrations set up in the piezoelectric ring 710, enabling the A0 mode to be set up in the transducer plate 712. Ultrasonic energy leaking from the plate 712 is reflected by the central reflector 716 to form a beam 718.

Referring to FIG. 12F, there is shown an overhead view of a transducer geometry that employs edge actuation-detection 730 and no reflection. In transducers implemented in accordance with FIG. 12F, leaky energy generated from a central leakage region 732 is focused onto a linear beam.

A preferred embodiment of a transducer configured in accordance with FIG. 12F is shown in FIG. 12G. The transducer of FIG. 12G includes a transducer plate 740 whose edges are coupled to an annular piezoelectric actuator-detector 742. The inner edges 744 of the piezoelectric 742 are not in contact with the transducer plate 740, which enables the entire plate 740 to flex in response to normal vibrations set up in the piezoelectric 742. As a result, A0 mode Lamb waves are set up in the plate 740 in response to appropriate excitation of the piezoelectric 742. This transducer configuration provides leaky energy 746 at a predetermined leak angle θ(f) that is focused on a line that passes through the center of and is normal to the plane of the plate 740 and the piezoelectric 742. A support 748, which could be formed from silicon or some other micromachinable material, is bonded to the piezoelectric 742 in such a fashion that a cavity 750 is created beneath the plate 740 that allows all energy to be transferred from the top face of the plate. This support 748 increases the excitation bandwidth of the PZT due to loading and acts like a substrate, increasing the efficiency of the transducer.

Referring to FIG. 12H, there is shown a schematic, overhead view of a transducer that employs central, rectangular actuation-detection 760 and edge reflection 762. In embodiments designed in accordance with FIG. 12H, ultrasonic energy exited by the central actuator 760 leaks from a leakage region 764. The leaked energy is reflected from the edge reflectors 762 to form a substantially perpendicular beam.

Referring to FIG. 12I, there is shown a rectangular transducer geometry where the actuator-detector consists of electrodes 770 bonded to one side of a transducer plate 772 spaced from a silicon back electrode 774. By modulating an electrostatic field placed across the electrodes 770, 774, the plate 772 is induced to flex at an appropriate frequency for generating A0 mode Lamb waves. Reflectors 776 machined from the same piece of material as the plate 772 transform the leaky energy 778 into normal beams 779. In a preferred embodiment, the material used to form the back electrode and the plate/reflector is <100> silicon, which has high attenuation and enables the reflector and back electrode surfaces to be formed by standard etching or micromachining processes.

Referring to FIG. 12J, there is shown a micromachined flow detector that includes top and bottom halves 780a, 780b. Each half 780 has a peripherally-supported transducer plate region 782 in which Lamb waves can propagate. A fluid (e.g., a gas) whose flow and/or pressure is to be measured is introduced via passages 789 between the halves 780a, 780b with a direction of flow along the X—X' axis. In the illustrated embodiment, the halves 780 are bonded together in alternate embodiments the halves 780 could be separated (e.g. see FIG. 12L) so the fluid can flow freely between the halves. When excited, a transmitter 784a bonded to the top half 780a causes leaky acoustic energy 786 to be emitted towards the bottom half 780b with some components along the direction of flow of the fluid whose flow is being measured. The leaky waves 786 set up the A0 Lamb wave mode 788 in the bottom plate 782b, which propagates towards the receiver 784b. The receiver 782b can measure the shift in the resonance frequency of the transmitter/receiver pair 782a/782b and/or the velocity change of the received Lamb wave 788, either of which can be used to determine the rate of flow of the fluid. The receiver 782b can also measure the amplitude of the Lamb wave 788, which enables fluid pressure to be determined. These parameters (i.e., resonance frequency, velocity and amplitude) are influenced by fluid flow along the direction of the leaky ultrasonic energy 786. Of course, the flow detector can operate in a mirror symmetrical fashion for fluid flowing in the opposite direction.

Referring to FIG. 12K, there is shown a top view of an alternate embodiment of the transducer of FIG. 12J. This embodiment includes two transmitters T1 and T4 mounted on the top plate 782a and two receivers R2 and R3 mounted on the bottom plate 782b. The transmitter T4 and the receiver R2, which correspond respectively to the transmitter 784a and the receiver 784b (FIG. 12J), measure flow and/or pressure as described above. The transmitter T1 and the receiver R3, which are not shown in FIG. 12J, are configured to measure only the temperature of the fluid flow. This is because T1 and R3 are positioned so their axis is perpendicular to the flow direction, meaning that leaky ultrasonic waves excited by T1 and traveling to R3 have no components parallel to the flow direction and therefore are unaffected by the fluid flow (of course, the amplitude of the received Lamb waves is still influenced by the pressure of the fluid). As a result, any resonance frequency shift or velocity changes measured by R3 are due to temperature changes only. The temperature measured by T1 and R3 can be used to calibrate the flow and pressure measurements of T2 and R4.

Referring to FIG. 13A, there is shown a plot of the impulse response of a leaky wave transducer that employs PZT-buffer rod excitation with a small Hertzian contact area and a cylindrical reflector for focused beam formation (i.e., a transducer similar to the embodiment of FIG. 12A). In particular, the impulse response of FIG. 13A was generated for a 20 μm plate of <100> silicon, which has its maximum attenuation in the 450–550 kHz range. The impulse response of FIG. 13A shows the following system advantages:

1) short impulse response as compared to prior art capacitive/resonance air transducers (transducers that consist of a flexible metallic diaphragm and an inflexible backplate) and composite transducers (transducers made of piezoelectrics and polymers); and 2) high signal to noise ratio (SNR) as compared to conventional PZT transducers.

Due to their short impulse response, the transducers of the present invention can be used for pulse-echo operation wherein a Lamb wave excited by a pulse can be processed twice: (1) on its initial arrival at a receiver and (2) upon its second (echo) arrival at the same receiver following a reflection. Pulse-echo operation is not possible when the Lamb wave has a long impulse response that obscures the arrival of the echo at the same receiver, which is typically the case for prior art air transducers.

In particular, prior resonance air transducers have small bandwidths and therefore long impulse responses. Prior PZT air transducers require many impedance matching layers to compensate for the large acoustic impedance difference between air and the PZT material. These impedance matching layers produce high insertion losses that render a PZT air transducer useless over even short distances unless it is operated over a narrow bandwidth, resulting in a long impulse response.

As for the high SNR provided by the present invention, this is made possible by selecting a transducer configuration that is sub-optimal for efficiency but which has high SNR (and bandwidth). This tradeoff is not generally possible with conventional PZT air transducers because of their losses, which result in a choice between low SNRs (caused by insertion losses) or narrow bandwidths.

Referring to FIG. 1 3B, there is shown a plot of the response of the same system to a five cycle tone burst input at 575 kHz. At this frequency the above-described transducer configuration is sub-optimal given the maximum attenuation range (450–550 kHz) of the <100> silicon used in the transducer plate. The signal to noise ratio for this sub-optimal configuration is about 32 dB. Given this SNR, the ultrasonic signal can be received across large distances (on the order of 10's of cm) with very little receiver gain. For example, using the embodiment characterized by FIGS. 13A and 13B, the transmission of ultrasound energy at 1.2 MHz over a distance of 4.5 cm requires an input signal of only 100–200mV with no gain at the receiver. These results are due to extremely low system losses of as little as 16 dB, including insertion losses and losses due to diffraction and attenuation in air, and represent vast improvements over the performance of prior art air transducers.

In summary, the devices of the present invention provide broader bandwidth and higher efficiency than prior art leaky wave transducers and can be implemented in geometries suitable to micromachining techniques necessary to provide high frequency ultrasound generation and detection in air. The devices of the present invention also advantageously employ reflectors of varying geometries to form beams from or to focus the leaky energy.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

For example, other embodiments can include signal processing techniques to improve transducer performance, including special signals to undo dispersion and matched filter techniques. Circular rings or linear arrays can be used for excitation with phasing for compact signals and multi-layered plates can be employed to provide wide bandwidth and efficiency.

What is claimed is:

1. A leaky wave transducer configured to provide high efficiency ultrasonic leakage into a fluid medium having low acoustic impedance, comprising:
   a plate of a material in which an A0 Lamb wave mode excited therein (a) is dispersive with a range of phase velocities that approximately encompasses the velocity of sound in the fluid medium and (b) which has a high attenuation;
   said plate having a thickness d such that the product fd of the thickness d and frequency f of the A0 Lamb wave mode determines a plate attenuation/bandwidth mode selected from (a) very high attenuation with narrow bandwidth or (b) the high attenuation with wide bandwidth, wherein the very high attenuation approximately equals peak attenuation and the high attenuation includes a range of attenuation values near but not encompassing the peak attenuation with high absolute values and small variation across the range; and
   a plate length l such that the product $\alpha l$ of the length l and a leak coefficient $\alpha$ equals 1.

2. A leaky wave transducer as in claim 1, further comprising a thick substrate disposed less than a half wavelength from the plate to lower the attenuation of the plate and increase the efficiency of the plate.

3. The leaky wave transducer of claim 2 in which the thick substrate is spaced from the plate a distance in the range $0.4\lambda_{fluid} > dgap > 0.1\lambda_{fluid}$, where $\lambda_{fluid}$ is the wavelength of the ultrasonic leakage in the fluid media.

4. A leaky wave transducer as in claim 1 including a reflector configured and positioned to intercept and reflect energy leaking from the plate.

5. A leaky wave transducer as in claim 4 wherein the reflector comprises a single reflecting face.

6. A leaky wave transducer as in claim 4 wherein the reflector comprises a structure to correct dispersion of the leak energy at different frequencies so the resulting beam includes the different frequencies at approximately same angles of propagation.

7. A leaky wave transducer as in claim 6 wherein the structure is selected from (a) a multifacet reflector or (b) a diffraction grating.

8. A leaky wave transducer as in claim 6 wherein the leaky plate has a variable thickness, wherein the reflector comprises a structure to correct dispersion of the leak energy at different frequencies so the resulting beam includes the different frequencies at approximately same angles of propagation and at predetermined spacings within the beam.

9. A leaky wave transducer as in claim 6 wherein the plate and the reflector are circularly symmetrical and the reflector is formed with multiple reflecting facets to focus the leak energy onto a point.

10. A leaky wave transducer as in claim 6 wherein the plate and the reflector are circularly symmetrical and the reflector is formed with a single reflecting face to focus the leak energy onto a line.

11. The leaky wave transducer as in claim 1 wherein the plate material is selected from the group consisting of: silicon, silicon dioxide, silicon nitride, piezoelectric material, or a composite of any combination of silicon, silicon dioxide, silicon nitride and piezoelectric material.

12. The leaky wave transducer as in claim 1 wherein the plate material includes micro-pores drilled therein to reduce the density of the plate material.

13. The leaky wave transducer of claim 1 wherein the plate material includes microstructures formed therein to reduce the density of the transducer material.

14. The leaky wave transducer as in claim 1, wherein the plate material has varying thickness.

15. The leaky wave transducer as in claim 1 wherein the plate material is a composite selected to improve the leakage and the bandwidth of the transducer as compared to a homogeneous transducer.

16. A leakage plate fashioned using micromachining techniques from a material with a high leakage attenuation, the leakage plate having dimensions including a thickness d selected so that the high leakage attenuation occurs at a frequency f and a length l characterized by the expression $\alpha l=1$, where "$\alpha$" is a leak coefficient; such that when the leakage plate is immersed in a low impedance fluid medium and an A0 Lamb wave mode with a characteristic frequency equal to the frequency f and a phase velocity that approximates the velocity of sound in the low impedance fluid medium is excited in the leakage plate by an actuator, the leakage plate will leak ultrasonic energy into the low impedance fluid medium.

17. The leakage plate of claim 16, wherein:
   the A0 Lamb wave mode has a range of phase velocities that approximately encompasses the velocity of sound in the fluid medium; and the product fd of the frequency f of the A0 Lamb wave mode and the thickness d determines a plate attenuation/bandwidth mode selected from (a) very high attenuation with narrow bandwidth or (b) the high attenuation with wide bandwidth, wherein the very high attenuation approximately equals peak attenuation and the high attenuation includes a range of attenuation values near but not encompassing the peak attenuation with high absolute values and small variation across the range.

18. A leaky wave fluid transducer, comprising:

a leakage plate fashioned using micromachining techniques from a material with a high leakage attenuation, the leakage plate having dimensions including a thickness d selected so that the high leakage attenuation occurs at a frequency f and a length l characterized by the expression $\alpha l=1$, where "$\alpha$" is a leak coefficient; such that, when the leakage plate is immersed in a low impedance fluid medium and an A0 Lamb wave mode with a characteristic frequency equal to the frequency f and a phase velocity that approximates the velocity of sound in the low impedance fluid medium is excited in the leakage plate, the leakage plate will leak ultrasonic energy into the low impedance fluid medium; and an actuator to excite the Lamb waves in the plate at the frequency f.

19. The leaky wave fluid transducer of claim 18, wherein the act a piezoelectric transducer; and a buffer rod with a first end bonded to the piezoelectric transducer and a second pointed end that makes a Hertzian contact with the plate;

such that, when electrically energized, the piezoelectric transducer sets up longitudinal waves that travel through the butter rod toward the plate, the pointed end coupling the longitudinal waves into the plate as Lamb waves at the frequency f.

20. The leaky wave fluid transducer of claim 18, wherein the actuator is configured to excite the Lamb waves using an electrostatic actuation mechanism comprising a pair of electrodes across which a modulated electrostatic potential is established, one of the pair being attached to the plate and a second of the pair being attached to a rigid beam or substrate near the plate.

21. The leaky wave fluid transducer of claim 18, wherein the actuator is configured to excite the Lamb waves using an interdigital transduction mechanism comprising electrically conductive IDT finders bonded to one side of the plate.

22. The leaky wave fluid transducer of claim 18, wherein the actuator comprises piezoelectric material bonded directly to the plate.

23. The leaky wave fluid transducer of claim 18, wherein the actuator is configured to detect the Lamb waves propagating in the plate.

24. The leaky wave fluid transducer of claim 18, wherein:

the A0 Lamb wave mode has a range of phase velocities that approximately encompasses the velocity of sound in the fluid medium, and the product fd of the frequency f of the A0 Lamb wave mode and the thickness d determines a plate attenuation/bandwidth mode selected from (a) very high attenuation with narrow bandwidth or (b) the high attenuation with wide bandwidth, wherein the very high attenuation approximately equals peak attenuation and the high attenuation includes a range of attenuation values near the peak attenuation with high absolute values and small variation across the range.

25. The leaky wave fluid transducer of claim 24, wherein the actuator is annular in shape and is configured to excite the Lamb waves from an edge position so that the leak energy leaks from a plate leak region inside the actuator-detector towards the center of the plate and is focused onto a beam perpendicular to the center.

26. The leaky wave fluid transducer of claim 24, further comprising a reflector configured to intercept and reflect the leak energy into a beam that is substantially perpendicular to the plane of the plate.

27. The leaky wave fluid transducer of claim 26, wherein the reflector is annular in shape and the actuator is configured to excite the Lamb Weaves from a central position so that the leak energy leaks from a plate leak region between said reflector and said actuator and reflects from at least one reflective face of the reflector to form a beam that is substantially perpendicular to the plane of the plate.

28. The leaky wave fluid transducer of claim 26, wherein the actuator is annular in shape and the reflector is positioned at a central position, the actuator being configured to excite the Lamb waves from an edge position so that the leak energy leaks from a plate leak region between the reflector and the actuator and reflects from at least one reflective face of the reflector to form a beam that is substantially perpendicular to the plane of the plate.

29. The leaky wave fluid transducer of claim 26, wherein:

the actuator, reflector and plate are rectangular;

the actuator excites the Lamb waves from a central position; and the reflector comprises a plurality of reflecting elements, each positioned at an edge of the plate to intercept leak energy triggered by the Lamb waves that leak from respective leak regions between said actuator and said reflector elements, the reflector elements being configured to reflect the leak energy to form respective beams substantially perpendicular to the plane of the plate.

30. The leaky wave fluid transducer of claim 29, wherein the plate and the reflector are micromachined.

31. The leaky wave fluid transducer of claim 30, wherein:

the plate is supported only by its edges; and the actuator is bonded to one side of the plate at a central position and excites the Lamb waves using electrostatic forces that cause the plate to flex at its center.

32. The leaky wave fluid transducer of claim 18, wherein:

the plate is supported only by its edges; and the actuator comprises a transmitter bonded to a first side of an unsupported portion of the plate, the transmitter being configured to excite Lamb waves in the plate, energy from which leaks from a second side of the plate opposite the first side;

the transmitter and plate forming a first half of a flow/pressure detector whose second half comprises an identical second half actuator that serves its a receiver and second half plate oriented with respect to the first half such that the energy leaking from the first half excites Lamb waves in the second half plate that are detected by the receiver, the receiver thereby indicating flow rate/pressure of a fluid flow between the first and second halves at least partially coincident with the energy leaking from the first half.

33. The leaky wave fluid transducer of claim 32, further comprising:

a second transmitter bonded to the first half;

a second receiver bonded to the second half;

the second transmitter being configured to excite Lamb waves in the first half plate, energy from which leaks towards the second half;

the second receiver being oriented with respect to the second transmitter such that the energy leaking from the first half plate due to action of the second transmitter excites Lamb waves in the second half plate that are detected by the second receiver; and the second transmitter and receiver beings positioned so that the leaky energy excited by the second transmitter and received by the second receiver via Lamb waves set up in the second half plate are insensitive to flow rate/pressure of the fluid flow but are sensitive to temperature of the fluid flow.

34. The leaky wave fluid transducer of claim 33, wherein the second transmitter and receiver provide temperature readings that are used to calibrate the flow rate/pressure measurements made by the flow rate/pressure-indicating transmitter and receiver.

* * * * *